US00PP23695P3

(12) United States Plant Patent
Zaiger et al.

(10) Patent No.: US PP23,695 P3
(45) Date of Patent: Jul. 2, 2013

(54) INTERSPECIFIC TREE NAMED 'COUNTRY COT'

(50) Latin Name: ***Prunus* species**
Varietal Denomination: Country Cot

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 388 days.

(21) Appl. No.: 12/931,058

(22) Filed: Jan. 24, 2011

(65) Prior Publication Data

US 2012/0192321 P1 Jul. 26, 2012

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

| | | | | | |
|---|---|---|---|---|---|
| PP2,877 | P | * | 4/1969 | Anderson | Plt./186 |
| PP2,964 | P | * | 1/1970 | Merrill | Plt./198 |
| PP6,673 | P | * | 3/1989 | Williams | Plt./116 |
| PP10,292 | P | * | 3/1998 | Zaiger et al. | Plt./180 |
| PP12,409 | P2 | * | 2/2002 | Zaiger et al. | Plt./180 |
| PP12,936 | P2 | * | 9/2002 | Zaiger et al. | Plt./180 |
| PP22,740 | P2 | * | 5/2012 | Zaiger et al. | Plt./180 |

* cited by examiner

*Primary Examiner* — Wendy C Haas

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1) A regular and productive bearer of large freestone fruit.
2) Fruit having an attractive orange skin and flesh color.
3) Fruit having firm flesh with good storage and shelf life.
4) Fruit having good flavor and eating quality.
5) Vigorous, upright tree growth.

1 Drawing Sheet

Botanical classification: *Prunus* species.
Variety denomination: 'Country Cot'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plums, apricots, peaches and interspecifics, which are known to us, and mentioned herein, 'Honey Rich' Interspecific (U.S. Plant Pat. No. 10,292), 'Patterson' Apricot (U.S. Plant Pat. No. 2,877), 'Flavor Supreme' Interspecific (U.S. Plant Pat. No. 6,673), 'O'Henry' Peach (U.S. Plant Pat. No. 2,964) and the proprietary interspecifics '178LM586', '122LE654', '12ZB628' and '14GD84'.

STATEMENT REGARDING FEDERALLY SPONSORED RESEARCH AND DEVELOPMENT

Not applicable.

ORIGIN OF THE VARIETY

The new and distinct variety of interspecific tree comprised of the following species *Prunus armeniaca, Prunus salicina* and *Prunus persica* was originated by us in our experimental orchard located near Modesto, Calif. as a first generation cross between our proprietary interspecific seedlings '178LM586' and '12ZB628'. The seed parent (178LM586) originated from the cross of the following parents; 'Honey Rich' Interspecific (U.S. Plant Pat. No. 10,292) and our proprietary interspecific '122LE654'. The pollen parent (12ZB628) originated from crosses of the following parents; 'Patterson' Apricot (U.S. Plant Pat. No. 2,877), 'Flavor Supreme' Interspecific (U.S. Plant Pat. No. 6,763), 'O'Henry' Peach (U.S. Plant Pat. No. 2,964) and our proprietary interspecific '14GD84'. A large number of these first generation crosses were grown and budded on older trees of 'Nemaguard' Rootstock (non-patented) to induce earlier maturity and fruit evaluations. One budded seedling exhibited desirable fruit and tree growth characteristics and was selected in 2005 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree [(Apricot×Plumcot)×(Apricot×Plumcot]×[(Apricot×Plumcot)×(Peach×Plum)] is of large size, vigorous, upright growth and a productive and regular bearer of large, orange flesh fruit with good flavor and eating quality. The fruit is further characterized by having an attractive orange skin color and firm flesh with good handling and shipping quality. In comparison to its seed parent (178LM586) the fruit of the new variety is larger in size and is approximately 2 days later in maturity. In comparison to its pollen parent (12ZB628) the new variety has a darker orange flesh and skin color and is approximately 14 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color.

Tree:

*Size.*—Large, usually pruned to 3 to 3.5 meters in height and width for economical harvesting of fruit. Varies with different cultural practices.

*Vigor.*—Vigorous, growth of 1.5 to 2 meters in height the first growing season. Varies with fertility and type of soil, climatic conditions and cultural practices.

*Form.*—Upright, usually pruned to vase shape.

*Branching habit.*—Upright, crotch angle approximately 35°, increases with heavy crop load.

*Productivity.*—Productive, thinning and spacing of fruit desirable. Fruit set varies with climatic conditions during blooming period.

*Bearer.*—Regular, has set an adequate crop 5 consecutive years. No alternate bearing observed.

*Fertility.*—Partially self-fertile, pollinator recommended.

*Density.*—Medium dense, usually pruned to vase shape to allow more sunlight to center of tree to enhance fruit color and health of fruit spurs.

*Hardiness.*—Hardy in all stone fruit growing areas of California. Tree grown in USDA Hardiness Zone 9. Winter chilling requirement of approximately 350 hours at or below 45° F.

Trunk:

*Size.*—Large. Average circumference 50.8 cm at 27.9 cm above ground.

*Stocky.*—Medium stocky.

*Texture.*—Medium shaggy, increases with age of growth.

*Color.*—Varies from 7.5YR 2/4 to 10YR 4/2.

Branches:

*Size.*—Medium. Average circumference 16.8 cm at 1.2 meters above ground. Crotch angle approximately 35°, increases with heavy crop load.

*Surface texture.*—New growth smooth. Mature growth medium rough, roughness increases with age.

*Lenticels.*—Size — medium. Average number 31 in a 25.8 square cm area of branch. Average length 2.8 mm. Average width 1.6 mm. Color varies from 10YR 7/8 to 10YR 6/8.

*Color.*—New growth varies from 5GY 4/8 to 5R 3/8 where exposed to the sun. Old growth varies from 5YR 2/2 to 7.5YR 2/2, varies with age of growth.

Leaves:

*Size.*—Large. Average length 89.1 mm. Average width 75.0 mm.

*Form.*—Varies from globose to ovate.

*Apex.*—Acuminate.

*Base.*—Obtuse.

*Margin.*—Serrate.

*Thickness.*—Medium.

*Surface texture.*—Upper surface relatively smooth, very slightly indented over midrib and leaf veins, glabrous. Lower surface relatively smooth except for small ridges caused by midrib and pinnate venation, glabrous.

*Petiole.*—Size — large. Average length 30.0 mm. Average width 1.6 mm. Longitudinally grooved. Surface glabrous. Color varies from 5R 3/8 to 5R 2/8.

*Glands.*—Type — globose. Size — medium. Average length 0.9 mm. Average diameter 0.6 mm. Number varies from 2 to 4, average number 3. Located primarily on the upper portion of the petiole and the base of the leaf blade. Color varies from 5R 2/8 to 2.5GY 5/4.

*Stipules.*—Average number 2 at the base of the petiole. Average length 6.0 mm. Margin — serrulate. Color varies from 2.5GY 7/6 to 5R 6/6.

*Color.*—Upper surface varies from 5GY 3/6 to 7.5GY 3/4. Lower surface varies from 5GY 4/4 to 7.5GY 4/4. Midvein color varies from 7.5R 4/10 to 2.5GY 7/6.

Flower buds:

*Size.*—Medium to large. Average length 15.8 mm. Average diameter 10.8 mm.

*Hardiness.*—Hardy with respect to California winters.

*Form.*—Conical, becoming slightly elongated just before opening.

*Pedicel.*—Short. Average length 2.0 mm. Average width 2.0 mm. Color varies from 5GY 7/8 to 5GY 6/6.

*Color.*—Varies from 7.5RP 6/12 to 7.5RP 9/2.

*Number of buds per spur.*—Varies from 2 to 9, average number 7. Varies with age of spur.

Flowers:

*Blooming period.*—Date of First Bloom Feb. 14, 2010. Date of Petal Fall Feb. 25, 2010, varies with climatic conditions.

*Size.*—Medium to large. Average height 18.2 mm. Average diameter 30.3 mm.

*Petals.*—Usually 5, alternately arranged to sepals. Size — large. Average length 14.3 mm. Average width 16.2 mm. Form — orbicular. Margin — sinuate. Color varies from 7.5RP 9/2 to 7.5RP 8/6, fades with age of flower. Both surfaces glabrous.

*Sepals.*—Usually 5, alternately arranged to the petals. Size — medium. Average length 6.7 mm. Average width 6.8 mm. Shape — ovate, apex rounded. Margin — entire. Both upper and lower surfaces glabrous. Color — upper surface varies from 5GY 8/4 to 2.5R 2/6. Lower surface varies from 5R 2/6 to 5R 2/8.

*Stamens.*—Average number per flower 29. Average filament length 12.3 mm. Filament color N 9.5/(white). Anther color varies from 5Y 8/10 to 5Y 7/10.

*Pollen.*—Present. Very little set under bag. Believed to be only partially self fertile, pollinator recommended. Color varies from 5Y 7/10 to 5Y 7/2.

*Pistil.*—Normally one. Surface pubescent. Average length 15.1 mm. Position of stigma even with the anthers. Color varies from 10Y 8.5/6 to 10Y 8/6.

*Fragrance.*—Slight.

*Color.*—Varies from 7.5RP 9/2 to 10RP 9/2, fades with age of flower.

*Number flowers per flower bud.*—Usually one, varies from 1 to 2.

*Pedicel.*—Average length 2.1 mm. Average width 2.2 mm. Color varies from 2.5GY 8/6 to 2.5GY 7/6.

Fruit:

*Maturity when described.*—Firm ripe.

*Date of first picking.*—May 20, 2010.

*Date of last picking.*—May 27, 2010, varies slightly with climatic conditions.

*Size.*—Large. Average diameter axially 71.8 mm. Average transversely in suture plane 60.1 mm. Average across suture plane 57.7 mm. Average weight 139.2 grams, average weight varies slightly with fertility of soil, amount of thinning and climatic conditions.

*Form.*—Elongated, slightly flatter toward suture plane.

*Suture.*—Distinct, extends from base to apex.

*Ventral surface.*—Lipped, well sealed.

*Apex.*—Slightly retuse.

*Base.*—Flat to slightly retuse.

*Stem cavity.*—Rounded to slightly elongated in suture plane. Average depth 3.9 mm. Average diameter 7.9 mm.

Stem:

*Size.*—Small. Average length 6.6 mm. Average diameter 2.9 mm.

*Color.*—Varies from 5GY 6/8 to 10Y 5/6.

Flesh:

*Ripens.*—Evenly.

*Texture.*—Firm, meaty.

*Fibers.*—Few, small, tender.

*Firmness.*—Firm, comparable to most commercial apricots.

*Aroma.*—Slight.

*Amydgalin.*—Undetected.

*Eating quality.*—Good.

*Flavor.*—Good, with good balance between acid and sugar.

*Juice.*—Moderate amount, enhances flavor.

*Brix.*—Average Brix 10.4°, varies slightly with amount of fruit per tree and climatic conditions.

*Color.*—Orange, 6.25YR 7/12. Pit cavity 6.25YR 6/12.

Skin:

*Thickness.*—Medium.

*Surface.*—Nearly smooth, very slightly waffled.

*Down.*—Light amount, very short in length.

*Tendency to crack.*—None.

*Color.*—Orange, varies from 5YR 5/10 to 7.5YR 5/10.

*Tenacity.*—Tenacious to flesh.

*Astringency.*—None.

Stone:

*Type.*—Freestone.

*Size.*—Large. Average length 44.2 mm. Average width 25.9 mm. Average thickness 14.7 mm.

*Form.*—Obovoid.

*Base.*—Usually flat, varies from flat to slightly rounded.

*Apex.*—Slight point. Average length 0.7 mm.

*Surface.*—Slightly pitted throughout. A shallow groove on each side of suture.

*Sides.*—Unequal, one side extending further from suture plane.

*Ridges.*—Small narrow ridge next to groove on each side of suture, extends from base to apex.

*Tendency to split.*—None.

*Color.*—Varies from 10YR 5/4 to 10YR 4/4 when dry.

*Pit cavity.*—Average length 53.0 mm. Average width 32.5 mm. Average depth 7.4 mm.

Kernel:

*Size.*—Large. Average length 24.7 mm. Average width 13.6 mm. Average depth 9.3 mm.

*Form.*—Ovate.

*Viability.*—Viable, complete embryo development.

*Skin.*—Color varies from 2.5Y 9/4 to 5.Y 9/2 when dry.

Use: Dessert.

*Market.*—Local and long distance.

Keeping quality: Good, held firm in cold storage 2 weeks at 38° to 42° F. without shriveling, internal breakdown of flesh or appreciable loss of eating quality.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

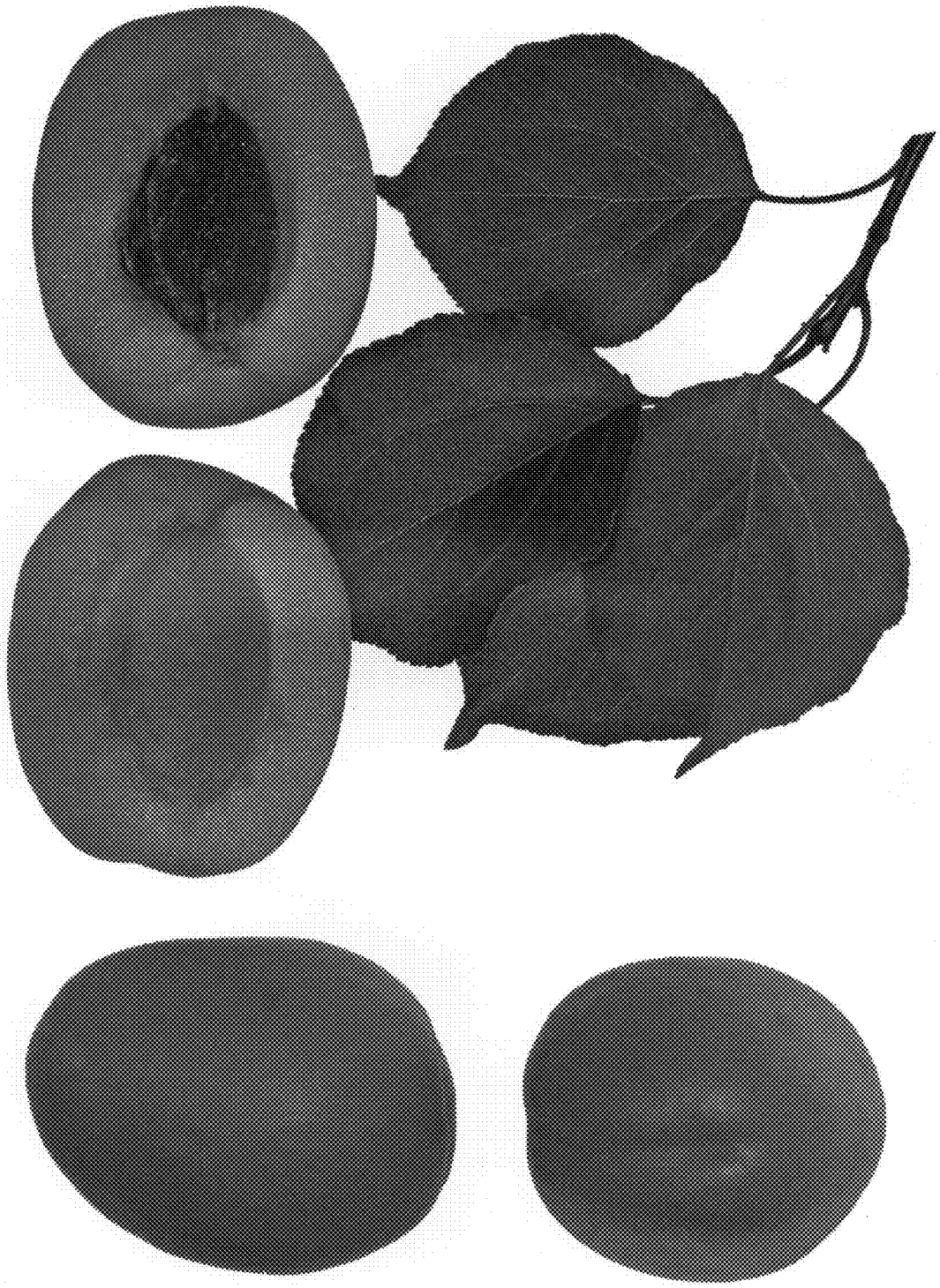

* * * * *